United States Patent [19]

Sprecker et al.

[11] Patent Number: 4,507,225

[45] Date of Patent: Mar. 26, 1985

[54] PROCESS FOR AUGMENTING OR ENHANCING THE AROMA OF PERFUME COMPOSITIONS, COLOGNES AND PERFUMED ARTICLES WITH 1-PHENYLPENTEN-4-ONE-1 AND METHYL HOMOLOGUES THEREOF

[75] Inventors: Mark A. Sprecker, Sea Bright; Marie R. Hanna, Hazlet, both of N.J.

[73] Assignee: International Flavors & Fragrances Inc., New York, N.Y.

[21] Appl. No.: 487,045

[22] Filed: Apr. 21, 1983

[51] Int. Cl.³ .................... A61K 7/46; C11D 9/30
[52] U.S. Cl. .................... 252/522 R; 252/522 A; 252/8.6; 252/174.11
[58] Field of Search .......... 252/522 R, 522 A, 174.11, 252/8.6

[56] References Cited

U.S. PATENT DOCUMENTS 4,372,881 2/1983 Ohloff et al. .................... 252/522 R

OTHER PUBLICATIONS

Buehler et al., "Survey of Organic Synthesis", (1974) p. 697.

Primary Examiner—Anton H. Sutto
Attorney, Agent, or Firm—Arthur L. Liberman

[57] ABSTRACT

Described for use in augmenting or enhancing the aroma of perfume compositions, perfumed articles and colognes is the genus of compounds having the structure:

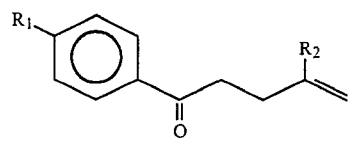

wherein one of $R_1$ or $R_2$ is methyl and the other of $R_1$ or $R_2$ is hydrogen or wherein both $R_1$ and $R_2$ are hydrogen, hereinafter referred to as 1-phenylpenten-4-one-1 and methyl homologues thereof.

10 Claims, 3 Drawing Figures

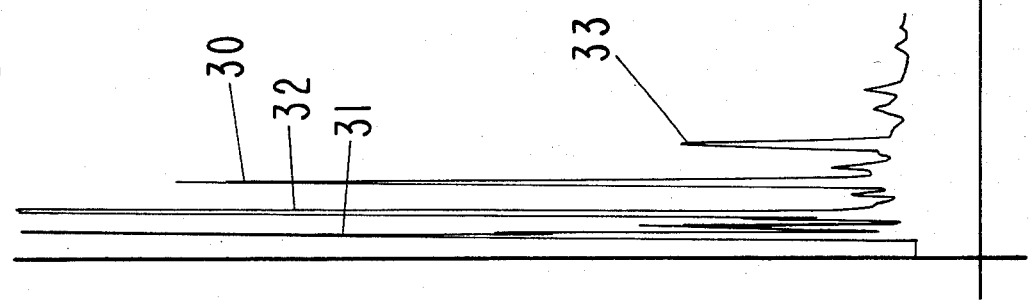
FIG.3 GLC PROFILE FOR EXAMPLE II. CRUDE
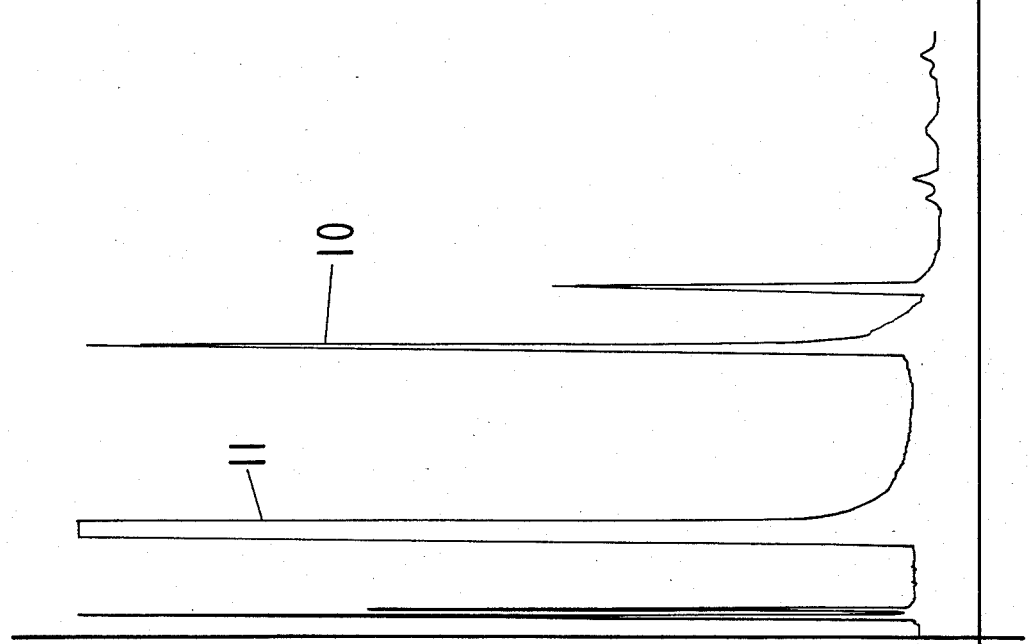
FIG.1 GLC PROFILE FOR EXAMPLE I. CRUDE

GLC PROFILE FOR FRACTION 6 OF EXAMPLE I.

PROCESS FOR AUGMENTING OR ENHANCING THE AROMA OF PERFUME COMPOSITIONS, COLOGNES AND PERFUMED ARTICLES WITH 1-PHENYLPENTEN-4-ONE-1 AND METHYL HOMOLOGUES THEREOF

BACKGROUND OF THE INVENTION

The present invention relates to 1-phenylpenten-4-one-1 and methyl homologues thereof having the generic structure:

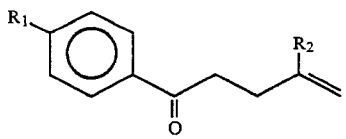

wherein one of $R_1$ or $R_2$ is methyl and the other of $R_1$ or $R_2$ is hydrogen or wherein both $R_1$ and $R_2$ are hydrogen and uses thereon in augmenting or enhancing the aroma of perfume compositions, colognes and perfumed articles.

There has been considerable work performed relating to substances which can be used to impart (or alter, modify or enhance) fragrances to (or in) perfume compositions, perfumes, colognes or perfumed articles. These substances are used to diminish the use of natural materials some of which may be in short supply and/or to provide more uniform properties in the finished product.

Green, elang, fruity, floral, rosey, animalic, opoponax, myrrh, mushroomy, hyacinth and lavender aroma nuances are particularly desirable in many types of perfume compositions, perfumes and perfumed articles, e.g. solid or liquid anionic, cationic, nonionic or zwitterionic detergents, fabric softener compositions, drier-added fabric softener articles, hair preparations and perfumed polymers.

Aryl alkenones and aryl alkadienones are known in perfumery for augmenting or enhancing the aroma of perfume compositions, colognes and perfumed articles. Thus, Arctander "Perfume and Flavor Chemicals (Aroma Chemicals)" Volumes I and II discloses the use in augmenting or enhancing perfumes of:

benzylidene acetone at monograph 318 of Volume I
3-methyl-4-phenyl-3-buten-2-one at monograph 2171 of Volume II
phenyl vinylethylene methylketone at monograph 2609 of Volume II thusly:

| 318: BENZYLIDENE ACETONE | |
|---|---|
| Methyl cinnamyl ketone.<br>Methyl styryl ketone.<br>Benzal acetone.<br>"Benzylidene ketone" (confusing name).<br>4-Phenyl-3-buten-2-one.<br>Cumaranol.<br>Exists in cis- and trans-form. (Commercial product is cis-isomer).<br>Note: Do not confuse with Benzyl acetone.<br>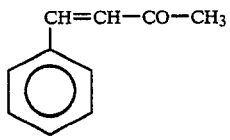<br>$C_{10}H_{10}O = 146.19$<br>Yellowish plate crystals. M.P. 42° C. (cis-isomer). M.P. 4° C. (trans-isomer).<br>Sp.Gr. 1.04. B.P. 262° C. Insoluble in water, soluble in alcohol and oils. Also soluble in sulfuric acid solution. | Sweet, but rather pungent odor with a creamy-floral note.<br>Occasionally used in perfumery for Sweet Pea (used to be a "must" in this type of fragrance), in Appleblossom, etc., often in combination with Neroli and Hyacinth bases.<br>Also used in flavors, particularly in Chocolate, Cocoa, Cherry, Fruit, Nut, Vanilla, etc.- but usually at very low concentration. Concentration in finished product will rarely exceed 0.2 to 0.5 ppm.<br>Prod. by Claisen condensation of Benzaldehyde and Acetone.<br>G.R.A.S. F.E.M.A. No. 2881.<br>Note: This ketone is repeatedly reported in trade literature as being strongly skin-irritating. It may be that its acceptance in food is approved only because of very low use-concentration.<br>4-19; 4-22; 5-165; 26-418; 30-179; 31-84; 95-170; 96-150; 100-139; B-VII-364; |

| 2171: 3-METHYL-4-PHENYL-3-BUTEN-2-ONE | |
|---|---|
| Benzylidene methyl ethyl ketone.<br>alpha-Methylcinnalylidene methylketone.<br>Benzylidene acetone methyl.<br>alpha-Methyl-alpha-benzalacetone.<br>"Malvone" (Agfa).<br>"Lavandozon" (Haarmann & Reimer).<br><br>Pale yellowish crystals.<br>Almost insoluble in water, soluble in alcohol and oils.<br>Sweet, fruity-caramellic, berry-like odor of good tenacity.<br>The effect is overall milder than that of Benzylidene acetone.<br>Sweet fruity, Cherry-Plum-like taste in dilutions below 10 ppm. Somewhat bitter at higher concentrations.<br>Trace amounts give interesting effects in Lavender fragrances. | 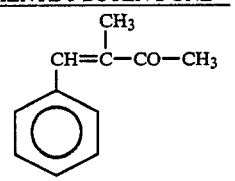<br>$C_{11}H_{12}O = 160.22$<br>This ketone finds some use in flavor compositions, although there are several chemicals of similar and better type available. Traces are used in many berry compositions, imitation Cherry, Vanilla and in Nut complexes.<br>The concentration will normally be as low as 0.5 to 3 ppm in the finished product.<br>Prod.: by condensation of Benzaldehyde with Methyl ethyl ketone.<br>G.R.A.S. F.E.M.A. No. 2734.<br>86-89; 4-19; |

| 2609: PHENYL VINYLETHYLENE METHYLKETONE | |
|---|---|
| Cinnamylidene acetone. | Warm-herbaceous, green-floral and very |

-continued

Phenyl-1,3-butadiene methylketone.
6-Phenyl-3,5-hexadien-2-one.
1-Phenylhexa-1,3-dien-5-one.
Chrystanthone.
Note: This material is not identical to the "Chrysanthone" identified as component of Chrysanthemum (plant).

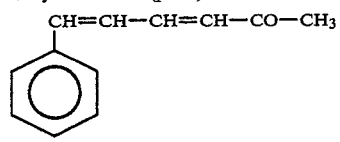

$C_{12}H_{12}O = 172.23$
White crystals. M.P. 68° C.
Practically insoluble in water, poorly soluble in cold alcohol, soluble in hot alcohol and most oils.

tenacious odor.
This material, rarely offered under its proper name, and often confused with the natural component of Chrysanthemum, is occasionally used as a fixative and floral-herbaceous blender/modifier in perfume compositions. Although it seems to be absolutely unknown in many perfumery circles, it is very highly appreciated by others, and it can give quite unique effects when used with experience. It gives very pleasant notes with Mimosa absolute, Ylang, Opopanax, Patchouli, etc. in the heavy Oriental-floral type.

Prod.: by condensation of Cinnamic aldehyde with Acetone.
36-1255; 68-990; 103-274; 163-65;

Cyclic unsaturated compounds bonded to 1-pentenoyl moieties are also known for use in augmenting or enhancing the aroma of perfumes, perfume compositions and perfumed articles. Thus, U.S. Pat. Nos. 4,264,467 issued on Apr. 28, 1981, 4,289,659 issued on Sept. 15, 1981 and 4,147,672 issued on Apr. 3, 1979 disclose compounds having the structures:

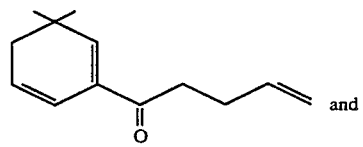 and

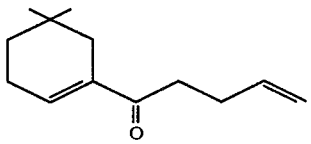

and the genus of compounds having the structure:

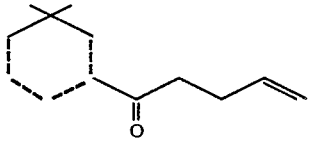

wherein the dashed lines represent carbon-carbon single bonds or one or two carbon-carbon double bonds.

None of the prior art disclosures, however, disclose the use in perfumery of the genus of compounds defined according to the structure:

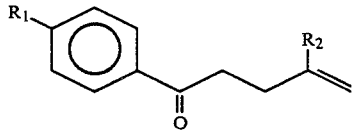

wherein one of $R_1$ or $R_2$ is methyl and the other of $R_1$ or $R_2$ is hydrogen or wherein both $R_1$ and $R_2$ are hydrogen.

The compound having the structure:

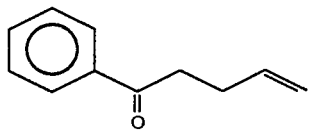

is a known compound and is disclosed at Beilstein H-373; EII 298 (abstracting J. M. Chem. Soc. Volume 58 (1936) 892 and J. M. Chem. Soc. Volume 60 (1938) 1905, 1911, disclosures of which are incorporated herein by reference).

BRIEF DESCRIPTION OF THE DRAWINGS

FIG. 1 is a GLC profile for the crude reaction product produced according to Example I containing the compound having the structure:

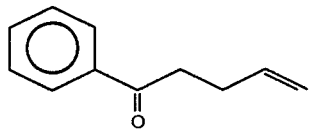

Figure 2:
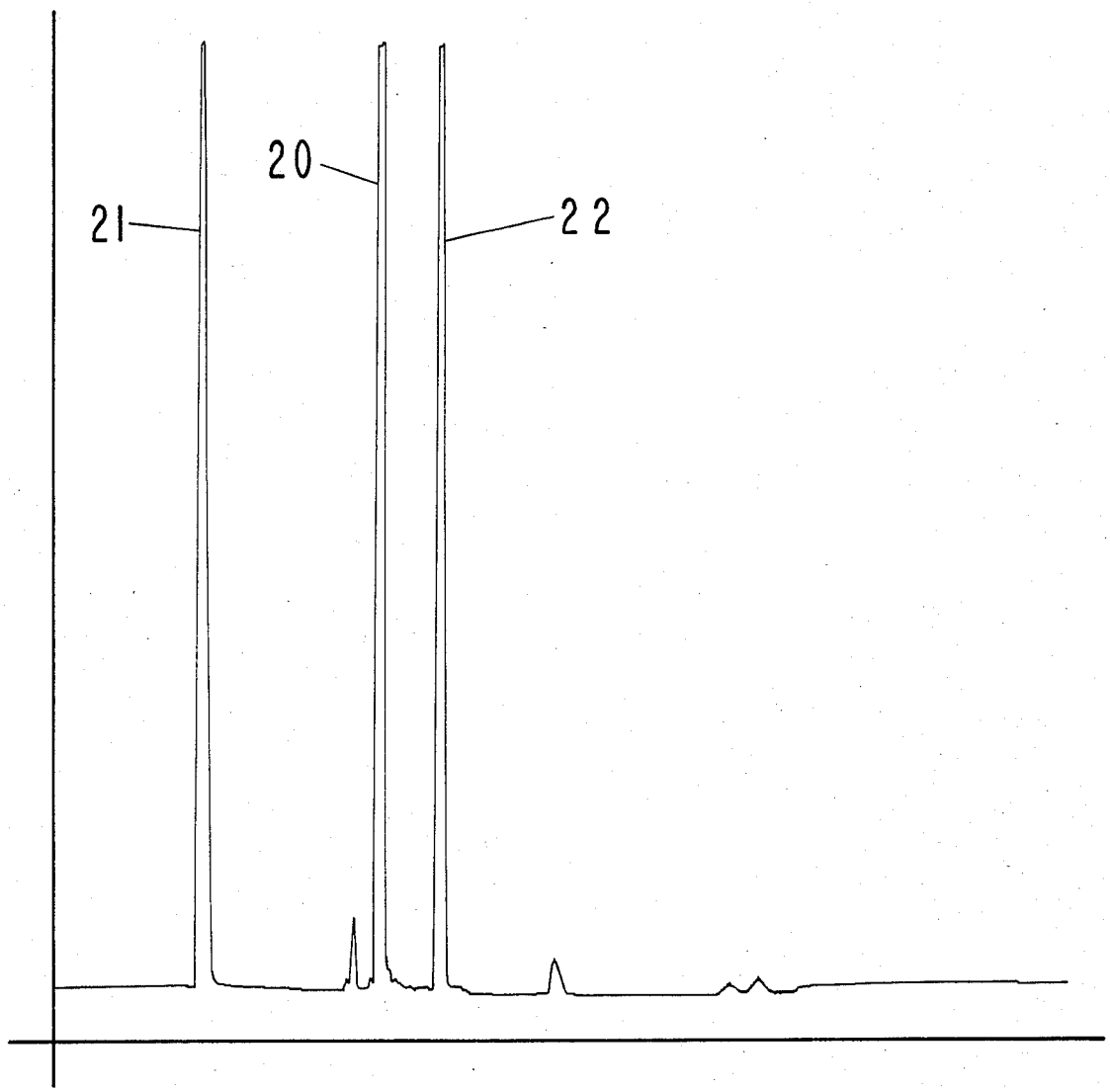

(conditions: SE-30 column programmed at 8° C. per minute from 140° C. up to 200° C.; then isothermal at 220° C.).

FIG. 2 is the GLC profile for fraction 6 of the distillation product of the reaction product of Example I containing the compound having the structure:

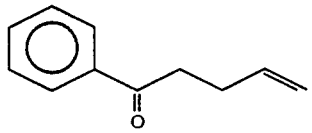

(conditions: SE-30 column programmed at 8° C. per minute from 140° C. up to 220° C.; then isothermal at 220° C.).

FIG. 3 is the GLC profile for the crude reaction product of Example II containing the compound having the structure:

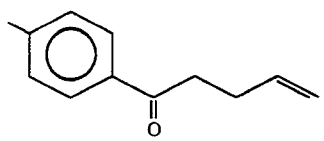

(conditions: SE-30 column programmed at 220° C. isothermal).

DETAILED DESCRIPTION OF THE DRAWINGS

In FIG. 1 (the GLC profile for the crude reaction product of Example I) the peak indicated by reference numeral "10" is the peak for the compound having the structure:

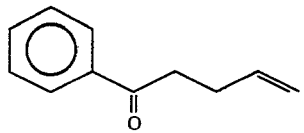

The peak indicated by reference numeral "11" is the peak for acetophenone.

In FIG. 2, the GLC profile for fraction 6 of the distillation product of the reaction product of Example I, the peak indicated by reference numeral "20" is the peak for the compound having the structure:

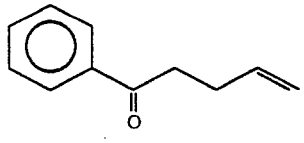

The peak indicated by reference numeral "21" is the peak for acetophenone. The peak indicated by reference numeral "22" is for the "diallyl" side product defined according to the structure:

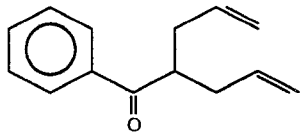

In FIG. 3, the GLC profile for the crude reaction product of Example II, the peak indicated by reference numeral "30" is the peak for the compound defined according to the structure:

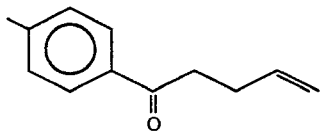

The peak indicated in FIG. 3 by the reference numeral "31" is the peak for allyl alcohol. The peak indicated by reference numeral "32" is the peak for p-methyl-acetophenone.

The peak indicated by reference numeral "33" is for the "diallyl" side product having the structure:

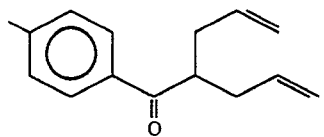

THE INVENTION

The present invention relates to the use of compounds defined according to the genus having the structure:

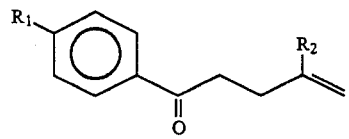

wherein one of $R_1$ or $R_2$ is hydrogen and the other is methyl or both of $R_1$ and $R_2$ are hydrogen for augmenting or enhancing green, elang, fruity, floral, rosey, animalic, opoponax, myrrh, mushroomy, hyacinth and lavender aroma nuances of perfume compositions, colognes and perfumed articles including solid or liquid anionic, cationic, nonionic or zwitterionic detergents, fabric softener compositions, fabric softener articles, hair preparations and perfumed polymers.

Compounds defined according to the genus:

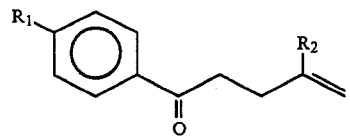

wherein one of $R_1$ or $R_2$ is hydrogen and the other is methyl or both of $R_1$ and $R_2$ are hydrogen may be formed by using means set forth in the prior art by reaction of allyl halides or allylic alcohols defined according to the structure:

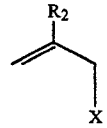

wherein $R_2$ is methyl or hydrogen and X represents hydroxyl, chloro or bromo with a compound defined according to the structure:

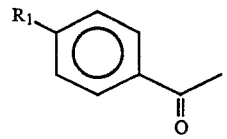

wherein $R_1$ is methyl or hydrogen. When X is chloro or bromo, the reaction takes place in the presence of base; preferably in the presence of a phase transfer agent using the techniques described in U.S. Pat. No. 4,045,489 issued on Aug. 30, 1977, the specification for which is incorporated by reference herein. Thus, in such a reaction involving the alkenylation of a ketone under the influence of a base, the reactants for the process and base are placed respectively in two immiscible phases; an organic phase and either (i) an aqueous base phase or (ii) a solid base phase with the reactant being located substantially entirely in the first mentioned organic phase and the base being located substantially entirely in the second mentioned phase; and adding to the two phase system a "phase transfer agent" which may one of several organic quarternary ammonium salts.

Specific examples of "phase transfer agents" useful in practicing the process for formation of the product useful in our invention are as follows:
tricapryl methyl ammonium chloride;
cetyl trimethyl ammonium bromide; or
benzyl trimethyl ammonium hydroxide.

In general, the "phase transfer agents" most preferred in such a process have the generic formula:

$$\left[ \begin{array}{c} R_1' \\ | \\ R_4'-N-R_2' \\ | \\ R_3' \end{array} \right] Z-$$

wherein at least one of $R_1'$, $R_2'$, $R_3'$ and $R_4'$ is $C_6-C_{14}$ aryl, $C_6-C_{10}$ aralkyl, $C_6-C_{20}$ alkyl, $C_6-C_{14}$ alkaryl and $C_6-C_{20}$ alkenyl and the other of $R_2'$, $R_3'$ and $R_4'$ is alkyl such as methyl, ethyl, n-propyl, i-propyl, 1-butyl, 2-butyl, 1-methyl-2-propyl, 1-pentyl and 1-octyl and Z- is an anion such as chloride, bromide and hydroxide.

The process used in producing the products useful in our invention is carried out in an expensive solvent which is inert to the reaction system such as toluene, benzene, o-xylene, m-xylene, p-xylene, ethyl benzene, n-hexane, cyclohexane, methylene chloride and o-dichlorobenzene. This process is carried out at a temperature in the range of from about 10° C. up to about 150° C. with a temperature range of 30°-120° C. being preferred. The reaction time is inversely proportional to the reaction temperature with lower reaction temperatures giving rise to greater reaction times; and accordingly, the reaction time ranges from about 30 minutes up to about 10 hours. The mole ratio of ketone:allylic halide is in the range of from 0.5:1.5 up to about 1.5:0.5 with a preferred ratio of ketone:allylic halide being from about 1:1 up to about 1:1.2. The mole ratio of base to allylic halide in the reaction mass may be in the range of from about 0.75:1 up to about 1.5:1 with a preferred ratio of base:allylic halide being from about 1:1 up to about 1.2:1.

The quantity of "phase transfer agent" in the reaction mass based on the amount of ketone in the reaction mass may vary from about 0.5 grams per mole of ketone up to 25 grams of "phase transfer agent" per mole of ketone with a preferred concentration of "phase transfer agent" being in the range of from about 2.5 up to about 7.5 grams of "phase transfer agent" per mole of ketone. The reaction is preferably carried out at atmospheric pressure since that is the most convenient condition. However, lower or higher pressures can be used without detrimentally affecting the ultimate yield of desired product. The particular base used in the reaction is not critical but preferred are sodium hydroxide and potassium hydroxide.

When X represents hydroxyl however, the reaction is carried out in the presence of a protonic acid, such as sulfuric acid or phosphoric acid or paratoluenesulfonic acid.

In carrying out either reaction, by-products are formed which may easily be separated from the reaction mass by means of standard fractional distillation techniques. These by-products are "diallylic" compounds defined according to the structure:

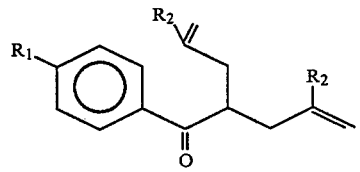

wherein one of $R_1$ or $R_2$ is hydrogen and the other of $R_1$ or $R_2$ is methyl or both of $R_1$ and $R_2$ are hydrogen, for example, compounds defined according to the structures:

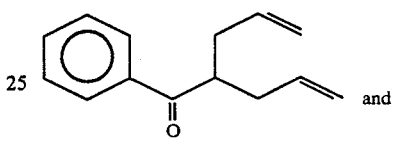 and

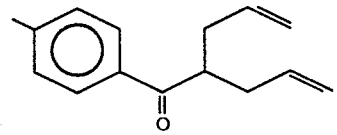

More specifically, the compounds produced according to the foregoing processes have the following organoleptic properties:

TABLE I

| Structure of Compound of Invention | Organoleptic Properties |
|---|---|
| 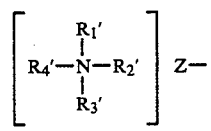 | A opoponax, myrrh, mushroomy aroma with floral, hyacinth, opoponax, myrrh and lavender nuances on dry-out. |
| 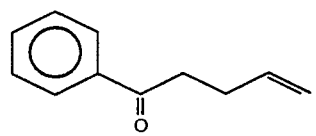 | A green, floral, elang, rosey, fruity and animalic aroma profile. |

The 1-phenylpenten-4-one-1 and methyl homologues thereof of our invention and one or more auxiliary perfume ingredients, including, for example, alcohols, aldehydes, ketones other than the 1-phenylpenten-4-one-1 and methyl homologues thereof of our invention, terpinic hydrocarbons, nitriles, esters, lactones, natural essential oils and synthetic essential oils, may be admixed so that the combined odors of the individual components produce a pleasant and desired fragrance, particularly and preferably in floral fragrances, e.g. hyacinth. Such perfume compositions usually contain (a) the main note or "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions it is the individual components which contribute to their particular olfactory characteristics, however the overall sensory effect of the perfume composition will be at least the sum total of the effect of each of the ingredients. Thus, the 1-phenyl-penten-4-one-1 and methyl homologues thereof of our invention can be used to alter, modify, or enhance the aroma characteristics of a perfume composition, for example, by utilizing or moderating the olfactory reaction contributed by another ingredient in the composition.

The 1-phenylpenten-4-one-1 and methyl homologues thereof of our invention which will be effective in perfume compositions as well as in perfumed articles and colognes depends on many factors including the other ingredients, their amounts and the effects which are desired. It has been found that perfume compositions containing as little as 0.01% of the 1-phenylpenten-4-one-1 and methyl homologues thereof of our invention or even less (e.g. 0.005%) can be used to impart a green, elang, fruity, floral, rosey, animalic, opoponax, myrrh, mushroom, hyacinth and lavender aroma to soaps, cosmetics or other products. The amount employed can range up to 70% of the fragrance components and will depend on considerations of cost, nature of the end product, the effect desired on the finished product and the particular fragrance sought.

The 1-phenylpenten-4-one-1 and methyl homologues thereof are useful (taken alone or together with other ingredients of perfume compositions) as olfactory components in detergents and soaps, space odorants and deodorants, perfumes, colognes, toilet water, bath preparations such as creams, deodorants, hand lotions and sun screens; powder such as talcs, dusting powders, face powders and the like. When used as olfactory components, as little as 1% of the 1-phenylpenten-4-one-1 and methyl homologues thereof of our invention will suffice to impart an intense, floral note to such formulations as rose and hyacinth formulations. Generally no more than 3% of the 1-phenylpenten-4-one-1 and methyl homologues thereof of our invention are required in the perfume composition.

Insofar as the use in perfumed articles is concerned, the 1-phenylpenten-4-one-1 and methyl homologues thereof of our invention may be used in perfumed articles such as solid or liquid anionic, cationic, nonionic or zwitterionic detergent compositions, fabric softener compositions, drier-added fabric softener articles and perfumed polymers in amounts of from about 0.5% up to about 5.0% based on the overall weight of the perfumed article.

In addition, the perfume composition or fragrance composition of our invention can contain a vehicle or carrier for the 1-phenylpenten-4-one-1 and methyl homologues thereof of our invention. The vehicle can be a liquid such as a non-toxic alcohol, e.g. ethyl alcohol, a non-toxic glycol, e.g. propylene glycol or the like. The carrier can also be an absorbent solid such as a gum (e.g. gum arabic, guar gum or xanthan gum) or components for encapsulating the composition (such as gelatin when using coacervation, or such as a urea formaldehyde polymer when forming a polymer around a liquid perfume center).

The following Examples I and II set forth processes for producing the products useful in the practice of our invention. The following Examples III et seq. serve to illustrate our invention.

All parts and percentages given herein are by weight unless otherwise specified.

EXAMPLE I

Preparation of Allyl Acetophenone

Reaction:

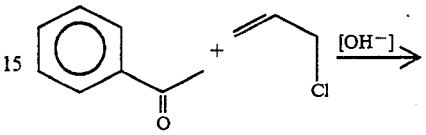

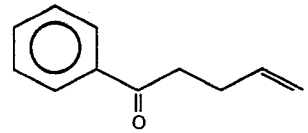

Into a 2.5 liter reaction vessel equipped with heating mantle, condenser, stirrer, thermometer and addition funnel is placed a solution of 120 grams of sodium hydroxide pellets (3 moles) in 180 ml water. 300 grams of toluene and 15 grams of tricapryl methyl ammonium chloride (ALIQUAT ®336, produced by Henkel Corporation of Minneapolis, Minn.) are then added to the mixture. The reaction mass is then heated to 80° C. and over a 1 hour period, a mixture of 1440 grams of acetophenone (12 moles) and 229.5 grams of allyl chloride (3 moles) is added to the reaction mass while refluxing. The reaction mass is then cooled to 90° C. and stirred at a temperature of 90° C. for a period of 11 hours.

The reaction mass is then mixed with 1 liter of cold water and transferred to a separatory funnel.

The organic layer is separated, washed neutral and the solvent is stripped off.

The residual oil is then fractionally distilled on a 2" Splash column yielding the following fractions:

| Fraction Number | Vapor Temp. (° C.) | Liquid Temp. (° C.) | Vacuum mm/Hg |
|---|---|---|---|
| 1 | 30/50 | 30/80 | |
| 2 | 80 | 90 | |
| 3 | 81 | 95 | 3 |
| 4 | 85 | 100 | 2 |
| 5 | 96 | 124 | 2 |
| 6 | 130 | 205 | 2 |

FIG. 1 is the GLC profile of the crude reaction product prior to distillation (conditions: SE-30 column programmed at 140°-220° C. at 32° C. per minute; then at 220° C., isothermal).

The peak indicated by reference numeral "10" is the peak for the product having the structure:

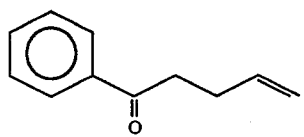

The peak indicated by reference numeral "11" is the peak for the acetophenone starting material.

FIG. 2 is the GLC profile for fraction 6 of the foregoing distillation. The peak indicated by reference numeral "20" is the peak for the product having the structure:

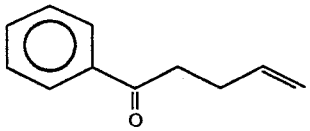

The peak indicated by reference numeral "21" is the peak for the starting material, acetophenone. The peak indicated by reference numeral "22" is the peak for the by-product of the reaction defined according to the structure:

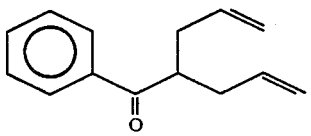

The resulting mixture may then be utilized "as is" for its organoleptic properties (an opoponax, myrrh and mushroomy aroma with floral, hyacinth, opoponax, myrrh and lavender nuances on dry-out) or the compound having the structure:

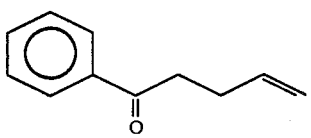

may be trapped out by commercial preparative column chromatography whereupon the pure compound having the structure:

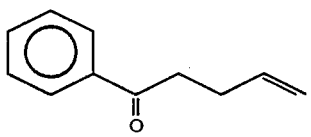

has an opoponax, myrrh aroma with intense floral, hyacinth, opoponax, myrrh and lavender nuances on dry-out.

EXAMPLE II

Preparation of Allyl-p-methylacetophenone

Reaction:

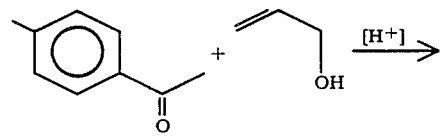

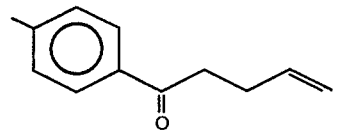

Into a 2 liter high-pressure autoclave is placed the following ingredients:
p-methylacetophenone, 402 grams (3 moles)
allyl alcohol, 261 grams (4.5 moles)
phosphoric acid, 10 grams.

The autoclave is sealed and heated to 200° C. at a pressure of 440 psig and maintained at that temperature and pressure with shaking over a period of 8 hours.

At the end of the 8 hour period, the autoclave is opened and the reaction mass is first distilled on a 2" Splash column yielding the following fractions:

| Fraction Number | Vapor Temp. (° C.) | Liquid Temp. (° C.) | Vacuum mm/Hg |
|---|---|---|---|
| 1 | 70/72 | 102/104 | 3 |
| 2 | 72 | 130 | 3 |
| 3 | 120 | 200 | 3 |

Fractions 2 and 3 are combined (weight: 151.3 grams) and redistilled on a 12"×1" Goodloe column yielding the following fractions:

| Fraction Number | Vapor Temp. (° C.) | Liquid Temp. (° C.) | Vacuum mm/Hg | Reflux Ratio |
|---|---|---|---|---|
| 1 | 66/72 | 91/105 | 3 | 9:1 |
| 2 | 72 | 116 | 3 | 9:1 |
| 3 | 74 | 121 | 2.8 | 9:1 |
| 4 | 105 | 122 | 2.8 | 9:1 |
| 5 | 106 | 126 | 2.8 | 9:1 |
| 6 | 108 | 126 | 2.8 | 9:1 |

FIG. 3 is the GLC profile of the crude product prior to distillation. The peak indicated by reference numeral "30" is the peak for the reaction product defined according to the structure:

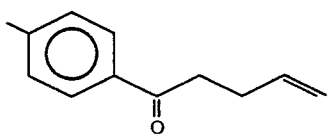

The peak indicated by reference numeral "31" is the peak for the starting material, allyl alcohol.

The peak indicated by reference numeral "32" is the peak for the starting material, p-methylacetophenone.

The peak indicated by reference numeral "33" is the peak for the by-product defined according to the structure:

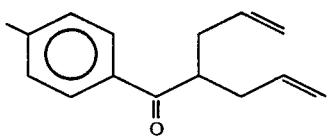

Bulked fractions 4-6 have an excellent green, floral, elang, rosey, fruity and animalic aroma making it useful for floral and "strawberry" fragrances. When bulked fractions 4-6 are purified using commercial liquid chromatographic techniques, the resulting pure product having the structure:

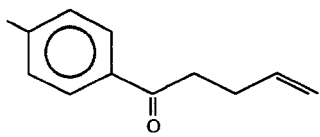

has a highly intense green, floral, elang aroma with musky, animalic undertones.

EXAMPLE III

Rose Perfume Formulation

The following formulation is prepared:

| Ingredients | Parts by Weight |
|---|---|
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| l-citronellal | 90.0 |
| Neryl acetate | 3.0 |
| Clove bud oil | 1.0 |
| Cadinene | 2.0 |
| Guaiene | 1.0 |
| Gum terpentine | 12.0 |
| Alpha-pinene | 1.0 |
| Myrcene | 5.0 |
| Limonene | 2.0 |
| p-cymene | 1.0 |

To the foregoing formulation 12 parts by weight of fraction 6 of the distillation product of the reaction product of Example I is added. This material contains a high proportion of the compound defined according to the structure:

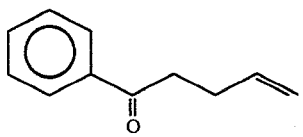

The resultant mixture has a much more natural-like rose note with excellent opoponax, myrrh, hyacinth and lavender nuances. Thus, the resulting perfume formulation can be described as rosey with opoponax, myrrh, hyacinth and lavender topnotes.

EXAMPLE IV

Rose Formulation

The following mixture is prepared:

| Ingredients | Parts by Weight |
|---|---|
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| l-citronellal | 90.0 |
| Neryl acetate | 3.0 |
| Clove bud oil | 1.0 |
| Cadinene | 2.0 |
| Guaiene | 1.0 |
| Gum terpentine | 12.0 |
| Alpha-pinene | 1.0 |
| Myrcene | 5.0 |
| Limonene | 2.0 |
| p-cymene | 1.0 | is added.

To the foregoing formulation 30 parts by weight of a mixture (bulked fractions 4-6) which is the distillation product of the reaction product of Example II containing a major proportion of the compound having the structure:

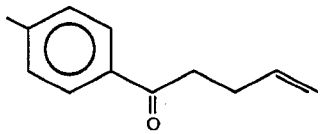

is added.

The resulting mixture has a much more natural-like "heady" aroma and the resulting perfume formulation can be described as "rose with an intense and long-lasting heady green, floral, elang, fruity aroma and animalic undertones".

EXAMPLE V

Preparation of a Soap

The perfumery materials set forth in Table II below are incorporated into a soap (LVU-1) at 0.1% by weight. After two weeks in an oven at 90° F., all of the materials set forth in Table II below showed no visual effect from the heat. On the other hand, the aroma of the materials in the soap are as set forth in Table II below:

TABLE II

| Perfumery Material | Aroma Characteristics |
|---|---|
| Pure material having the structure:<br><br>prepared according to Example I. | An opoponax, myrrh aroma with intense floral, hyacinth, opoponax, myrrh and lavender nuances on dry-out. |
| Pure material having the structure: | A highly intense green, floral, elang aroma with musky, animalic undertones. |

TABLE II-continued

| Perfumery Material | Aroma Characteristics |
| --- | --- |
| prepared according to Example II. | |
| Perfume composition of Example III. | Rosey with opoponax, myrrh, hyacinth and lavender topnotes. |
| Perfume composition of Example IV. | Rose with an intense and long-lasting heady green, floral, elang, fruity aroma and animalic undertones. |

EXAMPLE VI

Preparation of a Cosmetic Powder Composition

A cosmetic powder is prepared by mixing in a ball mill 100 grams of talcum powder with 2.5 grams of one of the materials set forth in Table II of Example V, supra. Each of the cosmetic powders produced has an aroma as set forth in Table II of Example V, supra.

EXAMPLE VII

Perfumed Liquid Detergent

Concentrated liquid detergents having aromas as set forth in Table II of Example V, supra (which detergents are produced from the lysine salt of n-dodecyl benzene sulfonic acid as more specifically described in U.S. Pat. No. 3,948,818 issued on Apr. 6, 1976, the specification for which is incorporated by reference herein) are prepared containing the various perfumery materials set forth in Table II of Example V, supra. They are prepared by adding and homogeneously mixing the appropriate quantity of the perfumery material set forth in Table II of Example V, supra in the liquid detergent. The detergents all possess aromas as set forth in Table II of Example V, supra, the intensity increasing with greater concentration of the perfumery material set forth in Table II of Example V, supra.

EXAMPLE VIII

Preparation of Colognes and Handkerchief Perfumes

The perfumery materials set forth in Table II of Example V, supra are each incorporated into colognes at concentrations of 1.5%, 2.0%, 2.5%, 3.0% and 4.0% in 70%, 75%, 80%, 85% and 90% aqueous ethanol samples; and into handkerchief perfumes at concentrations of 15%, 20,%, 25%, 30% and 35% (in 90% and 95% aqueous ethanol samples). Distinct and definitive aromas as set forth in Table II of Example V, supra are imparted to the colognes and to the handkerchief perfumes.

EXAMPLE IX

Preparation of a Detergent Composition

A total of 100 grams of a detergent powder (a nonionic detergent powder containing a proteolytic enzyme prepared according to Example 1 of Canadian Letters Pat. No. 985,190 issued on Mar. 9, 1976, the specification for which is incorporated by reference herein) is mixed with 0.15 grams of one of the perfumery materials set forth in Table II of Example V, until a substantially homogeneous composition is obtained. Each of the compositions so prepared has an excellent aroma as set forth in Table II of Example V, supra.

EXAMPLE X

Perfumed Liquid Detergents

Concentrated liquid detergents with aromas as set forth in Table II of Example V containing 0.10%, 0.15% and 0.20% of each of the perfumery materials of Table II of Example V, supra are prepared. They are prepared by adding and homogeneously admixing the appropriate quantity of perfumery material as set forth in Table II of Example V in the liquid detergent. The liquid detergents are all produced using anionic detergents containing a 50:50 mixture of sodium lauroyl sarcosinate and potassium n-methyl lauroyl tauride. The detergents all possess excellent fragrances as set forth in Table II of Example V, supra, the intensity increasing with greater concentration of perfumery material set forth in Table II of Example V, supra.

EXAMPLE XI

Preparation of a Detergent Composition

A total of 100 grams of detergent powder prepared according to U.S. Pat. No. 4,058,472, the specification for which is incorporated by reference herein, and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol, 35% sodium tetrapyrrole phosphate, 30% sodium carboxymethylcellulose and 7% of a starch is mixed with 0.15 grams of each of the perfume components (separate samples) as set forth in Table II of Example V, supra, until substantially homogeneous compositions are obtained. Each of the compositions so prepared has an excellent aroma as set forth in Table II of Example V, supra.

EXAMPLE XII

Preparation of Soap Compositions 100 grams of soap chips are prepared according to Example V of U.S. Pat. No. 4,058,490 issued on Nov. 15, 1977 (the specification for which is incorporated by reference herein) as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is drum dried. The resulting solid actives are then blended in a chip mixer with 10 lbs. water, 0.2 lb. titanium hydroxide."

The resulting mixture is admixed with 1 gram of each of the perfumery materials set forth in Table II of Example V, supra (separately). Each of the perfume soaps so prepared manifests an excellent aroma as set forth in Table II of Example V, supra.

EXAMPLE XIII

Utilizing the procedure of Example I of column 15 of U.S. Pat. No. 3,632,396 (the specification for which is incorporated by reference herein) a non-woven cloth substrate useful as drier-added fabric softening article of manufacture is prepared wherein the substrate, the substrate coating and the outer coating and the perfuming material are as follows:
1. a water "dissolvable" paper ("Dissolvo Paper");
2. Adogen 448 (m.p. about 140° F.) as the substrate coating; and
3. an outer coating having the following formulation (m.p. about 150° F.):
57% $C_{20-22}$ HAPS
22% isopropyl alcohol
20% antistatic agent
1% of each of the perfume materials (in separate sub examples) as set forth in Table II of Example V, supra and giving rise to aroma nuances as set forth in Table II of Example V, supra.

Fabric softening compositions prepared as set forth above and having the aroma characteristics set forth in Table II of Example V, supra, essentially consist of a substrate having a weight of about 3 grams per 100 square inches, a substrate coating of about 1.85 per 100 square inches of substrate and an outer coating of about 1.4 grams per 100 square inches of substrate thereby providing a total aromatized substrate and outer coating weight ratio of about 1:1 by weight of the substrate. The aromas as set forth in Table II of Example V, supra are imparted in a pleasant manner to the head space in the drier on operation thereof using said drier added fabric softening non-woven fabric.

EXAMPLE XIV

Perfumed Polymer

A perfumed polymer is prepared by mixing in an extruder at the level of 25% one of the perfumery substances as set forth in Table II of Example V and a 1:4 weight:weight mixture of polyepsilon caprolactone and low density polyethylene as set forth in application for U.S. Pat. Ser. No. 468,997 filed on Feb. 23, 1983, the specification for which is incorporated herein by reference. The resulting extruded polymers are pelletized and the resulting polymeric pellets are then manufactured into articles of manufacture such as garbage bags. The resulting garbage bags manifest excellent aromas as set forth in Table II of Example V, supra.

What is claimed is:

1. A process for augmenting or enhancing the aroma of a perfume composition, cologne or perfumed article comprising the step of adding to a perfume composition base, a cologne base or a perfumed article base, an aroma augmenting or enhancing quantity of at least one compound defined according to the structure:

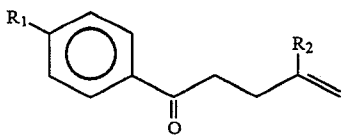

wherein $R_1$ and $R_2$ each represent methyl or hydrogen with the proviso that $R_1$ and $R_2$ are not both methyl.

2. The process of claim 1 wherein $R_1$ and $R_2$ are each hydrogen.

3. The process of claim 1 wherein $R_1$ is methyl and $R_2$ is hydrogen.

4. The process of claim 1 wherein $R_2$ is methyl and $R_1$ is hydrogen.

5. The process of claim 1 wherein the compound having the structure:

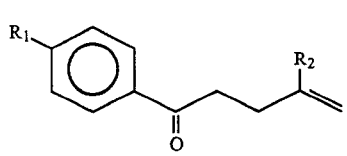

is added to a perfume composition.

6. A perfume composition comprising a perfume base and intimately admixed therewith an aroma augmenting or enhancing quantity of at least one compound defined according to the structure:

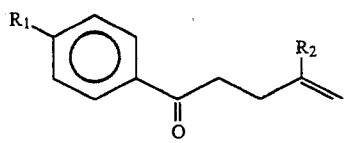

wherein $R_1$ and $R_2$ each represent methyl or hydrogen with the proviso that $R_1$ and $R_2$ are not both methyl.

7. The process of claim 1 wherein the compound having the structure:

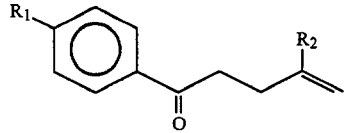

is added to a perfumed article and the perfumed article is a solid or liquid anionic, cationic, nonionic or zwitterionic detergent.

8. The process of claim 1 wherein the compound having the structure:

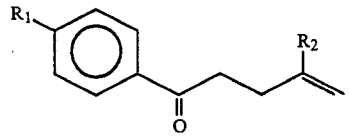

is added to a perfumed article and the perfumed article is a perfumed polymer.

9. The process of claim 1 wherein the compound having the structure:

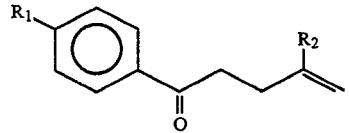

is added to a perfumed article and the perfumed article is a fabric softener composition or fabric softener article.

10. A cologne comprising water, ethanol and an aroma augmenting or enhancing quantity of at least one compound defined according to the structure:

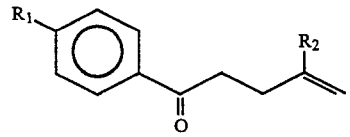

wherein $R_1$ and $R_2$ each represent methyl or hydrogen with the proviso that $R_1$ and $R_2$ are not both methyl.

* * * * *